US009201077B2

(12) United States Patent
Nett et al.

(10) Patent No.: US 9,201,077 B2
(45) Date of Patent: Dec. 1, 2015

(54) DIRECT ENZYME IMMUNOASSAY FOR MEASUREMENT OF SERUM PROGESTERONE LEVELS

(75) Inventors: Terry M. Nett, Bellvue, CO (US); Patrick M. McCue, Fort Collins, CO (US); Ryan M. Brooks, Middleburg, VA (US); Jason E. Bruemmer, Fort Collins, CO (US); David J. Denniston, Mead, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 576 days.

(21) Appl. No.: 12/844,231

(22) Filed: Jul. 27, 2010

(65) Prior Publication Data

US 2011/0020847 A1    Jan. 27, 2011

Related U.S. Application Data

(60) Provisional application No. 61/228,871, filed on Jul. 27, 2009.

(51) Int. Cl.
| | |
|---|---|
| *G01N 33/74* | (2006.01) |
| *G01N 33/543* | (2006.01) |
| *G01N 33/544* | (2006.01) |
| *G01N 33/551* | (2006.01) |
| *C07K 16/26* | (2006.01) |
| *G01N 33/53* | (2006.01) |

(52) U.S. Cl.
CPC .............. *G01N 33/743* (2013.01); *C07K 16/26* (2013.01); *G01N 33/5306* (2013.01); *G01N 33/543* (2013.01); *G01N 33/544* (2013.01); *G01N 33/54393* (2013.01); *G01N 33/551* (2013.01); *G01N 2333/575* (2013.01)

(58) Field of Classification Search
CPC ....... C07K 16/26; G01N 1/28; G01N 33/743; G01N 33/5306; G01N 33/543; G01N 33/54393; G01N 33/544; G01N 33/551; G01N 33/581; G01N 2333/575; Y10S 435/975; Y10S 436/814; Y10S 436/906
USPC .......... 435/7.1, 7.5, 7.91, 7.92, 7.93, 28, 975; 436/510, 518, 524, 528, 544, 547, 65, 436/174, 175, 176, 810, 814, 906, 177; 530/388.24, 389.2, 391.1, 391.3; 600/551
See application file for complete search history.

(56) References Cited

U.S. PATENT DOCUMENTS 4,720,455 A * 1/1988 Babu et al. ................... 435/7.93
7,189,520 B2 * 3/2007 Muldoon et al. ............... 435/7.1

FOREIGN PATENT DOCUMENTS

WO    89/02076 A1 *  3/1989

OTHER PUBLICATIONS

Colazo et al., 2007. Comparison of 2 enzyme immunoassays and a radioimmunoassay for mesurement of progesterone concentrations in bovine plasma, skim milk, and whole milk. Canadian J. Vet. Res. 72: 32-36.*
Goding, 1983. Monoclonal Antibodies: Principles and Practice, Academic Press, London. pp. 250-261.*
Carriere, P.D., et al. "Direct radioimmunoassay of progesterone in bovine plasma using danazol (17-alpha-2,4-pregnadien-20-yno(2,3-d)isoxazol-17-ol) as a displacing agent." Can J Vet Res. Jul. 1994;58(3):230-3.
Chan, D.W., et al. "The chemistry of human transcortin. The effects of pH, urea, salt, and temperature on the binding of cortisol and progesterone." Arch Biochem Biophys. Aug. 1977;182(2):437-42.
De Boever, J., et al. "Solid-phase chemiluminescence immunoassay for progesterone in unextracted serum." Clin Chem. Oct. 1984;30(10):1637-41.
Eckersall, P.D., et al. "The use of a bovine plasma progesterone ELISA kit to measure progesterone in equine, ovine and canine plasmas." Vet Rec. Jan. 3, 1987;120(1):5-8.
Giguere, S., et al. "Evaluation of two qualitative enzyme immunoassays for the rapid assessment of progesterone in equine plasma." Can Vet J. Oct. 1994;35(10):643-5.
Hatzidakis, G., et al. "Comparison of different antibody-conjugate derivatives for the development of a sensitive and specific progesterone assay." J Reprod Fertil. Mar. 1993;97(2):557-61.
Haynes, S.P., et al. "Radioimmunoassay of progesterone in unextracted serum." Clin Chem. 1980 Oct;26(11):1607-9.
Hinrichs, K., et al. "Use of an immediate, qualitative progesterone assay for determination of day of ovulation in an equine embryo transfer program." Theriogenology. 1988;29(5):1123-30.
McGinley, R., et al. "Analysis of progesterone in unextracted serum: a method using danazol [17 alpha-pregn-4-en-20-yno(2, 3-d) isoxazol-17-ol] a blocker of steroid binding to proteins." Steroids. Feb. 1979;33(2):127-38.
Munro, C., et al. "Development of a microtitre plate enzyme immunoassay for the determination of progesterone." J Endocrinol. Apr. 1984;101(1):41-9.
Pinto, C.R.F., et al. "Utilization of a semi-quantitative ELISA progesterone kit in broodmare management." Animal Reproduction Science, 2006;94:204-206.
Ratcliffe, W.A. Direct (non-extraction) serum assays for steroids. In: Hunter, W.M., et al. eds. "Immunoassays for clinical chemistry." 2nd Edition. Edinburgh; Mew York: Churchill Livingstone, 1983;401-409.
Ratcliffe, W.A. "Evaluation of four methods for the direct assay of progesterone in unextracted serum." Ann Clin Biochem. Sep. 1982;19(Pt 5):362-7.
Ratcliffe, W.A., et al. "Direct 125I-radioligand assays for serum progesterone compared with assays involving extraction of serum." Clin Chem. Jun. 1982;28(6):1314-8.
Relave, F., et al. "Accuracy of a rapid enzyme-linked immunosorbent assay to measure progesterone in mares." Can Vet J. Aug. 2007;48(8):823-6.
Rosner, W. "Plasma steroid-binding proteins." Endocrinol Metab Clin North Am. Dec. 1991;20(4):697-720.

(Continued)

*Primary Examiner* — Gail R Gabel
*Assistant Examiner* — James L Grun
(74) *Attorney, Agent, or Firm* — Kathleen D. Rigaut; Dann, Dorfman, Herrell and Skillman

(57) ABSTRACT

Compositions, methods and kits for determining progesterone levels in mares are disclosed.

16 Claims, 10 Drawing Sheets

(56) References Cited

OTHER PUBLICATIONS

Shrivastav, T.G., et al. "Direct radioimmunoassay for the measurement of serum progesterone using 3H as a label." J Immunoassay Immunochem. 2007;28(2):137-46.

Yoon, D.Y., et al. "Use of progesterone-3(O-carboxymethyl oxime)-horseradish peroxidase in a sensitive microtitreplate EIA and its application to a visual membrane EIA of progesterone." J Immunoassay. May 1995;16(2):137-53.

* cited by examiner

Standard Curve for Double Antibody Assay and homologous combination of Antibody and Conjugate

Standard Curve for Extracted ELISA

DIRECT ENZYME IMMUNOASSAY FOR MEASUREMENT OF SERUM PROGESTERONE LEVELS

This application claims priority to U.S. Provisional Application 61/228,871 filed Jul. 27, 2009, the entire contents being incorporated herein by reference.

FIELD OF THE INVENTION

The present invention is directed to the fields of immunoassay and animal reproduction. More specifically, the invention provides compositions, methods and kits for accurate and direct measurement of progesterone levels in serum samples.

BACKGROUND OF THE INVENTION

Several publications and patent documents are cited throughout the specification in order to describe the state of the art to which this invention pertains. Each of these citations is incorporated herein by reference as though set forth in full.

Progesterone is secreted by the corpus luteum (CL) of the ovaries, placenta, and potentially the adrenal glands. Production of progesterone by the CL is supported primarily by luteinizing hormone (LH) secreted from the anterior pituitary gland. This primary source of progesterone changes during pregnancy in the mare as the fetal-placental unit begins producing progestins around days 50 to 70 (Samper J S, Pycock J F, McKinnon A O. Current therapy in equine reproduction. Philadelphia, Pa.: Saunders Elsevier, 2007; xvi, 492 s). Serum concentrations of progesterone are high, (>10 ng/ml), for about the first 150 days of gestation due to production by both primary and secondary corpora lutea (Fowden A L, Forhead A J, Ousey J C. The endocrinology of equine parturition. Experimental and Clinical Endocrinology & Diabetes 2008; 116: 393-403). Progesterone is nearly non-detectable in maternal blood after 200 days of gestation although it is present in the placenta and fetal circulation (Silver M. Placental Progestagens in the Sheep and Horse and the Changes Leading to Parturition. Experimental and Clinical Endocrinology 1994; 102: 203-211). Pregnancy is maintained in late gestation by various progestins, including $5\alpha$-DHP, $3\beta$-5P, $\beta\beta$-diol, $20\alpha$-5P and $\beta\alpha$-diol.

Progesterone has multiple functions in the mare. Production of this hormone is required for the maintenance of pregnancy. Progesterone produced from the corpus luteum that formed after ovulation is responsible for uterine secretions and physical embryo-uterine interactions such as embryo mobility, fixation, and orientation. In addition, both estrogen and progesterone are key components to positive- and negative-feedback loops that control the release of prolactin, FSH, and LH from the anterior pituitary as well as various other reproductive hormones (McKinnon A O, Voss J L. Equine reproduction. Ames, Iowa: Blackwell Publishing, 2005; xxv, 1137 p). The LH pulse-generating system is negatively impacted by progesterone in the mare.

Progesterone is metabolized very rapidly in the mare, primarily to $5\alpha$-pregnane derivatives. Progesterone is almost completely metabolized in one passage through the GI mucosa and liver. The metabolites are primarily excreted in the urine. Metabolic clearance rates of progesterone were not significantly different in anestrous, diestrous, ovariectomized, pregnant, or lactating mares.

Only about 1-3% of progesterone is free (ie. unbound) in the blood of mares. A majority of progesterone is bound to cortisol binding globulin (CBG) and albumin carrier proteins. The proportion of progesterone bound to CBG and albumin is somewhat controversial and may be species specific. In humans, it is reported that 80% of progesterone is bound to albumin and 18% to transcortin (CBG), while the remaining 2% is free. Once steroid hormones enter into the bloodstream via endogenous secretion or exogenous administration, they immediately interact with several plasma steroid-binding proteins. Albumin is a high-abundance protein with low steroid-binding affinity and specificity whereas CBG is a low abundance protein with high steroid-binding affinity and specificity. Plasma concentrations of CBG are much lower than that of albumin but CBG plays an important role in binding and transporting biologically active steroids in the blood. Cortisol binding globulin has a single steroid binding site with which it can bind either progesterone or cortisol with high affinity. Understanding the relationship between CBG and progesterone is of extreme importance to accurately measure total progesterone concentrations.

Progesterone is essential for the maintenance of pregnancy in the mare. Among other roles, progesterone induces the endometrium to conform to invasion of microcotyledons and gaseous exchange demands of the placenta, to stimulate endometrial glands to secrete "uterine milk" for the nourishment of the embryo, and to maintain quiescence of the myometrium (Allen W R. Luteal deficiency and embryo mortality in the mare. Reprod Domest Anim 2001; 36: 121-131; Silver M. Placental Progestagens in the Sheep and Horse and the Changes Leading to Parturition. Experimental and Clinical Endocrinology 1994; 102: 203-211). The mechanism used to ensure high blood concentrations of progesterone in the pregnant mare is different than other domestic species.

There are three sources of progestins throughout pregnancy in the mare. The initial corpus luteum that formed after the ovulation that resulted in the conceptus is solely responsible for the production of progesterone until approximately day 40. The progesterone secreted from the primary corpus luteum increases until about day 8 post ovulation at which point levels slowly begin to decrease until day 28 to 30. It is thought that the 1° CL may undergo partial regression though it does not completely regress until much later in gestation, contrary to initial belief. The 1° CL regresses along with the 2° CL around 180 to 220 days of gestation. It has been suggested that CL regression occurs as a result of the loss of the luteotropin equine chorionic gonadotropin (eCG). This is most likely not the case as eCG is nearly nondetectable at 120 days of gestation, long before the regression of primary and secondary corpora lutea.

Secondary corpora lutea form around day 40 of gestation and are a supplementary source of progesterone in the pregnant mare. They contribute to a dramatic increase in concentrations of serum progesterone. The formation of 2° CL coincides with the development of endometrial cups and subsequent secretion of equine chorionic gonadotropin (eCG), which has a luteotropic role. The number of 2° CL increase until approximately 140 days; however, the quantity of 2° CL varies greatly from mare to mare. There are two types of 2° CL, those arising from ovulation and those from luteinization without ovulation. Some refer to corpora lutea resulting from ovulation as secondary and those resulting from luteinization of anovulatory follicles as accessory. It is still unknown as to the proportion that results from ovulations compared to anovulatory luteinization although formation of 2° CL from ovulation is much more likely to occur between days 40 to 70 than after day 70. A majority of 2° CL are nearly identical in physical characteristics when compared to the 1° CL. All 2° CL regress around 180 to 220 days.

Low progesterone is of great concern in the pregnant mare. There are two main classifications that exist: 1) the absence of adequate endogenous progesterone secretion due to factors that affect the function of the CL, and 2) the inability of "normal" circulating progesterone levels to maintain pregnancy. Examples of the first include accidental $PGF_{2\alpha}$ administration, luteolysis resulting from endotoxemia, and failure of maternal recognition of pregnancy. Examples of the second include mares that consistently lose their pregnancy yet have normal serum progesterone levels, placentitis, and impending abortion due to stress in late gestation. Low luteal progesterone production may arise from a variety of mechanisms including primary corpus luteum insufficiency, luteolysis due to uterine inflammation (endometritis) and subsequent release of $PGF_{2\alpha}$, failure of mechanisms responsible for maternal recognition of pregnancy followed by luteolysis, luteolysis due to systemic endotoxemia, and stress. Luteal insufficiency or inadequate production of progesterone by the corpus luteum has been proposed as a cause of early pregnancy loss; however, there is very limited evidence to support primary luteal insufficiency as the true cause. In a study conducted by Irvine et al. (1990; Equine Veterinary Journal; 22: 104-106), it was found that out of 17 mares that exhibited early pregnancy loss, only one was associated with low progesterone levels in maternal circulation.

Accurate measurement of progesterone in the normal cycle is of interest to determine the phase of the estrous cycle (ie. estrus versus diestrus). This can be extremely beneficial if one is unable to ultrasound a mare or if a mare has "silent heats." Accordingly, a need exists in the art for the rapid and accurate detection of circulating progesterone levels in the mare in order to more closely monitor and also maintain pregnancy in subject animals.

SUMMARY OF THE INVENTION

In accordance with the present invention, a highly sensitive and accurate method for measuring progesterone concentration in a sample taken from a test subject is provided. An exemplary method entails obtaining a sample from the test subject, and contacting the sample with an agent which reduces the pH of the sample (step a). A known amount of tracer reagent consisting of progesterone operably linked to an enzyme (step b) and an immobilized antibody that specifically binds to and is specific for progesterone are provided. The immobilized antibody is then contacted with a stabilizing solution (step c). A known amount of the solution of step a) is contacted with a known amount of the tracer reagent of step b) in the presence of the immobilized antibody of step c) (step d). Unbound tracer is washed away from the solution of step d) and the amount of tracer reagent of step b) bound to the antibody of step c) is detected via competitive enzyme linked immunoabsorbent assay (step f) and the amount of progesterone present in the sample is calculated based on the results obtained in step f). In a preferred embodiment the sample is mare serum or plasma. Also preferred is immobilization of the anti-progesterone antibody onto a cuvette, such that the signal can be read in a spectrophotometer. The assay is extremely sensitive and is linear over the 0 to 4 ng/ml range. The method can be used to determine a variety of parameters, including without limitation, determination of normal luteal values, confirmation of ovulation, presence or absence of anovulatory follicles, identification of transitional mares, evaluation of progesterone augmentation therapies, evaluation of embryo transfer recipients, evaluation of progesterone levels in pregnant mares, activity of secondary corpora lutea, and failure of maternal recognition of pregnancy.

In yet another embodiment of the invention, a kit for practicing the method described above is provided. An exemplary kit contains solutions suitable for running an ELISA assay, stabilized progesterone-HRP conjugate, substrate solution, cuvettes comprising stabilized, immobilized anti-progesterone antibody, solutions useful to lower the pH of the serum sample, and progesterone standards indicative of a given state of estrus.

DETAILED DESCRIPTION OF THE INVENTION

Figure 1A:
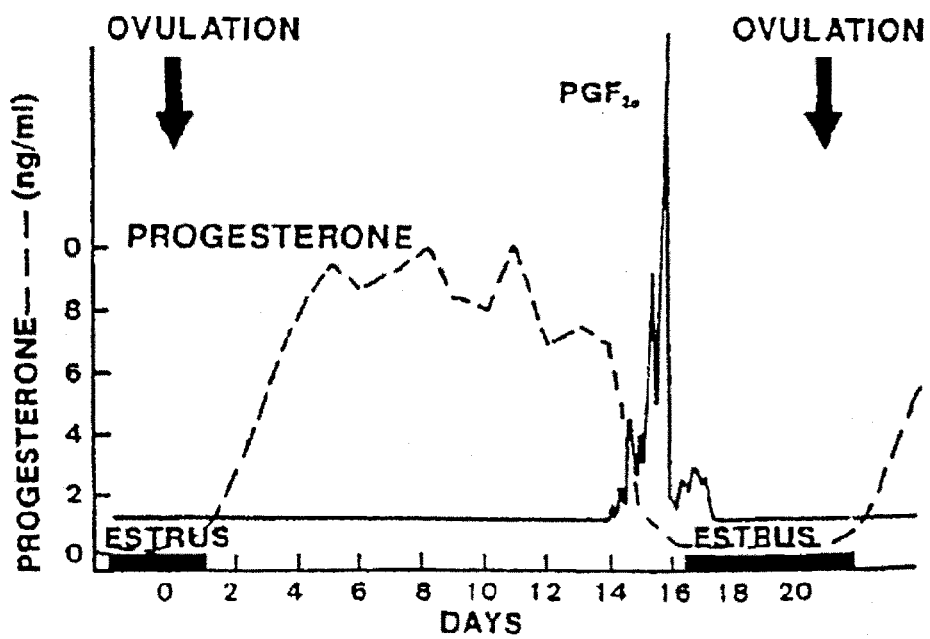
FIG. 1A is a graph showing progesterone and $PGF2\alpha$ concentration during the estrous cycle.
Figure 1B:
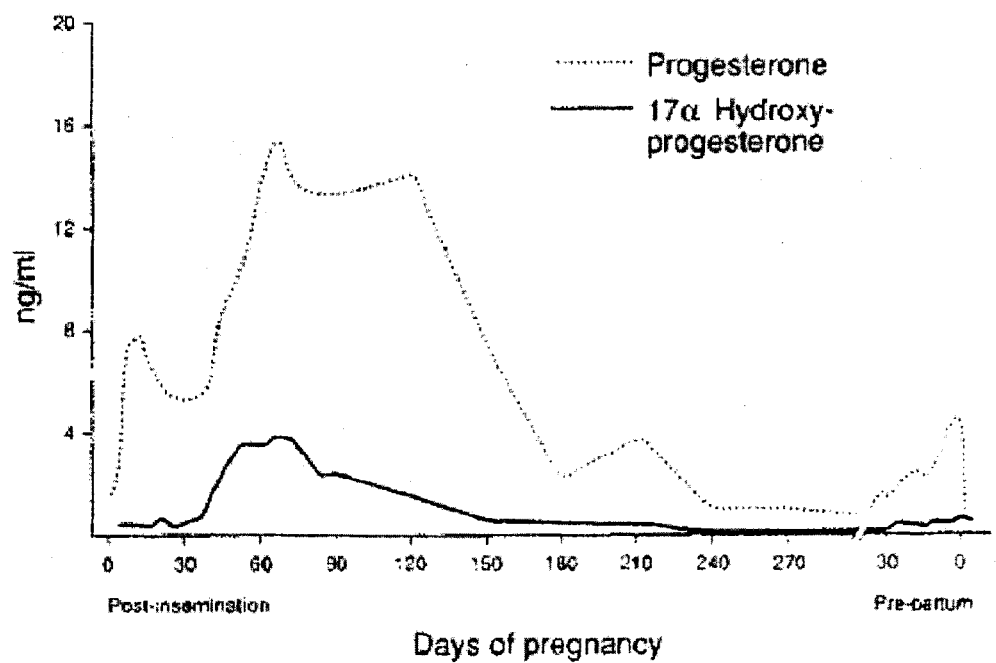
FIG. 1B is a graph showing progesterone concentration during gestation in the mare (Adapted from McKinnon et al., (2005).

Progesterone (P4) is a steroid hormone produced by the corpus luteum of the ovary and the placenta of the mare. Progesterone is required for the maintenance of pregnancy and an assessment of endogenous concentration has utility in many diagnostic applications related to equine breeding management. In accordance with the present invention, a direct enzyme-linked immunosorbent assay (ELISA) for the accurate measurement of P4 in serum of in the mare has been developed. The overall correlation between ELISA of non-extracted serum and radioimmunoassay (RIA) of extracted serum was high (r=0.81); and the correlation between ELISA and RIA for progesterone concentrations less than 5.0 ng/ml, the range most important for clinical diagnosis, was even greater (r=0.91). The direct ELISA assay thus can be used to advantage in the equine breeding industry as it will allow for diagnostic tests to determine the adequacy of corpus luteum function in a pregnant mare, presence or absence of luteal tissue, and assessment of the end of seasonal transition.

The following definitions are provided to facilitate the practice of the present invention.

As used herein, "mare" refers to female horses, including ponies.

As used herein, "cycling" refers to an animal that is experiencing an estrous cycle, i.e., is not pregnant and is not in seasonal anestrus (i.e. reproductive dormancy).

As used herein, "breeding" refers to methods known in the art that pertain to making a female animal pregnant. Such methods include natural breeding and artificial insemination.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', $F(ab')_2$, F(v), scFv, $scFv_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668). Dabs can be composed of a single variable light or heavy chain domain. In a certain embodiment of the invention, the variable light domain and/or variable heavy domain specific for progesterone are inserted into the backbone of the above mentioned antibody constructs. Methods for recombinantly producing antibodies are well-known in the art. For example, commercial vectors comprising constant genes to make IgGs from scFvs are provided by Lonza Biologics (Slough, United Kingdom).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

As used herein "binding partner" refers to a molecule that binds to an antigen, antibody, antibody/antigen complex or other molecule used in this invention. Preferred binding partners for antigens are antibodies specific to those antigens.

The phrase "solid support" refers to any solid surface including, without limitation, any chip (for example, silica-based, glass, or gold chip), cuvette, glass slide, membrane, test strip, bead, solid particle (for example, agarose, sepharose, polystyrene or magnetic bead), column (or column material), test tube, or microtiter dish. In preferred embodiments, the solid support is a cuvette which can be read in a spectrophotometer.

As used herein "immobilized on a cuvette" or "fixedly placed on a cuvette" with respect to a molecule means the molecule is attached to the cuvette such that flow of fluids across the cuvette during an assay process will not dislodge the molecule.

As used herein, "pregnancy testing" refers to testing for pregnancy and/or non-pregnancy.

As used herein, "non-pregnancy" refers to the state of not being detectably pregnant.

As used herein, "early-stage pregnancy" means to about day 35.

As used herein, "mid-stage pregnancy" means about day 35 to about day 200.

As used herein, "late stage pregnancy" means the period following mid-stage pregnancy.

As used herein, "whole blood" refers to blood as drawn. Whole blood contains a substantial amount of red blood cells, white blood cells and fibrin.

As used herein, "plasma" refers to unclotted blood with no substantial amount of cells. Plasma does contain clotting factors.

As used herein, "serum" refers to blood without a substantial amount of cells or clotting factors.

As used herein, "mareside" or "stallside" refers to an environment or location in which a domesticated animal is found (including on a breeding farm or in a veterinary clinic), particularly in contrast to a laboratory environment.

As used herein, "breeding cycle time" refers to the time between one breeding of an animal and the next breeding during the next estrous cycle of the same animal.

As used herein, "normal background level" of an antigen refers to the level of a selected antigen in a non-pregnant animal in a control sample taken during a time in an animal's estrous cycle or after breeding corresponding to the time of taking a test sample.

The phrases "affinity tag," "purification tag," and "epitope tag" may all refer to tags that can be used to effect the purification of a protein of interest. Purification/affinity/epitope tags are well known in the art (see Sambrook et al., 2001, Molecular Cloning, Cold Spring Harbor Laboratory) and include, but are not limited to: polyhistidine tags (e.g. 6×His), polyarginine tags, glutathione-S-transferase (GST), maltose binding protein (MBP), S-tag, influenza virus HA tag, thioredoxin, staphylococcal protein A tag, the FLAG™ epitope, AviTag epitope (for subsequent biotinylation), dihydrofolate reductase (DHFR), an antibody epitope (e.g., a sequence of amino acids recognized and bound by an antibody), and the c-myc epitope.

Test devices of this invention may be in the form of cartridges, dipsticks, cuvettes or other conformations known to the art. The test device may also be part of a kit which may contain instructions for use, instructions for comparison of test results with results of the same test done on non-pregnant animals, additional reagents, such as cells or fluids from non-pregnant animals, and other reagents known to the art.

A "tracer reagent" as used herein refers to a detectably labeled progesterone molecule.

Antibody supports and test membranes are also known to the art. In a preferred embodiment, the antibody supports are cuvettes. Alternatively, membranes to which the antibodies are removably, or fixedly attached may be employed. The assays provided by this invention may utilize polyclonal or monoclonal antibodies to the selected antigens. They may use the same or different polyclonal or monoclonal antibodies for capture and (or) detection. The antibodies may be labeled using labels known to the art. Preferably, the label is readily detectable. Preferably a sandwich assay is performed using an assay device such as a cartridge or a dipstick. Devices provided by this invention comprise detection and (or) capture antibodies, support for the antibodies, a means for contacting the antibodies with a sample from an animal, a means of detecting binding of the antibodies to the selected antigens, and optionally, flow control elements to confirm that the sample is properly flowing within the test device. The devices may also contain means for measuring the level of the selected antigens relative to the amount of background level of the selected antigens. Some of the devices also contain means for filtering serum or plasma from whole blood.

The competitive ELISA described herein requires that an antibody specific to progesterone is bound to a solid phase (e.g., a cuvette) and that remaining binding sites on the solid phase are blocked with non-reactive protein solutions. Following washing of unbound antibody and blocking solutions, the antibodies are challenged with a solution containing a mixture of a known amount of a tracer comprised of progesterone covalently linked to a ligand, and a known volume of serum or plasma. The solid phase containing the antibody bound to the tracer and progesterone, is washed as before with a buffer, and then exposed to a second binding conjugate containing an enzyme. In some cases the tracer contains the enzyme (e.g. HRP, AP) itself. This method causes a competition for specific antibody binding sites between the tracer and progesterone, such that once the substrate of the enzyme is added, decrease in signal from the pre-determined level is directly related to the level of progesterone in the sample.

Methods of Using the Compositions and Kits of the Invention

Measuring progesterone in the normal cycle is of interest to determine the phase of the estrous cycle (ie. estrus versus diestrus). This can be extremely beneficial if one is unable to ultrasound a mare or if a mare has "silent heats." Plasma progesterone levels increase significantly within the first 12 hours of ovulation and are >2.0 ng/ml 48 hours after ovulation. Evaluation of serial serum samples can be used to determine the day of ovulation.

There are several pathologic reproductive conditions that arise in the mare. These include persistent anovulatory follicles, luteinized anovulatory follicles, questionable ovulations, granulosa cell tumors and many more. In a study performed at Colorado State University on mares with ovulation failure, serum progesterone concentrations were below 1 ng/ml in 14.3% of mares. These mares had persistent anovulatory follicles (PAF), which were characterized by the prolonged presence of a follicle with an absence of echogenic particles in the follicular lumen. In contrast, 85% of anovulatory mares had elevated progesterone levels. These mares had luteinized anovulatory follicles (LAF) characterized by a progressive increase in echogenicity of the follicular lumen. Being able to assess the progesterone concentration would allow one to determine if the structure was a PAF or LAF and subsequently determine whether it would respond to prostaglandins. Administration of prostaglandins to LAF's resulted in a rapid decline of plasma progesterone levels to <1.0 ng/ml within 48 hours. The ability to assess the concentration of progesterone in a mare would inherently allow one to determine luteal function which would also answer the questionable ovulation as well as other situation such as whether a mare has a mature CL that will respond to prostaglandins and allow her to be short-cycled. When diagnosing a granulosa cell tumor in a mare an endocrine panel of inhibin, testosterone and progesterone is most commonly performed. Progesterone is a helpful indicator as concentrations are almost always low (<1 ng/ml), consistent with the absence of luteal tissue. If progesterone is greater than 1 ng/ml this is suggestive that a mare does not have a GCT as the tumor does not produce progesterone and affected mares usually do not develop follicles and ovulate.

Elevated levels of progesterone during gestation are important as progesterone is required for the maintenance of pregnancy. Mares that had pregnancy loss between days 11 and 15 showed significantly lower progesterone concentrations than mares that were able to maintain pregnancy. A drop in progesterone was a rare cause of pregnancy loss between days 17 to 42. Whether a mare has low progesterone due to original formation of a small CL or has a CL that seems to be regressing due to failure of maternal recognition of pregnancy or for other reasons, the resulting inadequate levels of progesterone will most likely cause a loss of pregnancy. Assessment of the concentration of progesterone would allow one to determine if levels were sufficient to maintain pregnancy. If levels are considered to be low, exogenous progesterone supplementation may be required. The minimal level of progesterone considered to be adequate to maintain pregnancy in the first trimester is 4 ng/ml. If a mare has endogenous progesterone levels below 4 ng/ml, supplementation is suggested and if levels are above 4 ng/ml the mare theoretically has adequate progesterone to maintain pregnancy.

Clinical applications for a progesterone test include assessment of progesterone levels during pregnancy, determination of the presence or absence of a corpora luteum in mares that are acyclic or during the spring transition period, confirmation of ovulation, confirmation of progesterone levels in mares that do not display behavioral signs of estrus ("silent heat"), and determination of progesterone patterns in infertile mares.

Kits for practicing the direct immunoassay are also within the scope of the present invention and are described further hereinbelow. An exemplary kit contains antibody coated cuvettes, buffers, progesterone standards and apparatus for performing the assay and optionally, a densimeter device for reading the output signal which is indicative of progesterone concentration in the test animal.

The following examples are provided to illustrate certain embodiments of the invention. They are not intended to limit the invention in any way.

EXAMPLE I

Direct Immunoassay for Progesterone in Serum

In this example, the development of a quantitative and sensitive progesterone ELISA assay suitable for use on non-extracted equine serum or plasma is described. This highly sensitive assay has been adapted from a 96-well plate format to a single cuvette system and thus allows for quantification of progesterone by a commercially available spectrophotometer. The progesterone ELISA assay is based on the principle of competitive binding between progesterone in the sample and progesterone-HRP conjugate in the presence of a constant amount of rabbit anti-progesterone. This sensitive assay can be used to detect progesterone levels between 0 and 10 ng/ml, and avoids the requirement for steroid extraction.

The following materials and methods are provided to facilitate the practice of Example 1.

ELISA Assay Protocols for Microtiter Plates

Preparation of Antiserum (Anti-$P_4$) and Conjugate ($P_4$-HRP)

Anti-progesterone antibody is acquired as an undiluted stock solution in a volume of 400 µl from the University of California, Davis. A volume of 200 µl is added to 1.8 mls of coating buffer, creating a 1:10 dilution.

Conjugate is acquired as an undiluted stock solution in a volume of 250 µl. A volume of 50 µl of stock conjugate is added to 4.95 ml of EIA buffer, creating a 1:100 dilution. A further dilution is required to achieve a final dilution of 1:200, 000, which is working concentration of conjugate used in the assay.

Coating Microtitre (96-well) Plates

Microtiter Plates (96-well) are coated with antiserum prior to use. One aliquot of 1:10 antiserum and diluted with coating buffer to a concentration or 1:5,000. A volume of 50 µl is added to all wells with the exception of wells 1A and 1B, which will serve as blanks. The plate is tilted and gently tapped to disperse antibody and cover entire well evenly. The plate is covered or sealed with acetate plate sealer and placed in a resealable bag. The coated plate is then stored at 4° C. for a minimum of 24 hours and maximum of 3 to 4 weeks.

Preparation of Standards for the Direct (Non-Extracted) ELISA:

A pooled sample of 200 mls of gelding or ovariectomized mare serum is collected. A total of 1.0 mg of purified progesterone is added to 10 ml EtOH. An initial dilution of 100 µl of progesterone in EtOH into 900 µl pooled serum is made. Subsequently, additional serial dilutions are made by adding specific volumes of this first dilution into specific volumes of pooled progesterone-free serum yielding final concentrations of 20, 10, 5.0, 2.5, 1.25, 0.625, and 0 ng/ml.

The Direct ELISA for Progesterone

A volume of 1.0 ml of standards and samples are placed into 12×75 mm glass test tubes, to which 500 µl 1 N HCl is added. The tubes are vortexed for 20 seconds. A volume of 500 µl EIA buffer is added into each test tube and the tube is again vortexed for 20 seconds. The 96-well plate is inverted to remove fluid contents and subsequently washed 5 times with wash solution. The plate is dried by firmly tapping upside down on paper towel. A volume of 50 µl EIA buffer is added across the entire plate. Then, a volume of 10 µl of standards are added in quadruplicate to columns 3-10. Samples (10 µl) are added in duplicate to columns 3-10. Subsequently, a volume of 50 µl of working conjugate is added across the entire plate. The plate is then covered and sealed with acetate plate sealer and allowed to incubate for 1 hour and 45 minutes at room temperature. The plate is then inverted to remove well contents and then washed 5 times with wash solution. A volume of 100 µl ABTS substrate is added across the entire plate. The plate is allowed to incubate for 45 minutes at room temperature. A volume of 100 µl stop solution is added across the entire plate. The plate is then transferred into an automated plate reader and 'read' at 415 nm.

Contents and Protocol for Cuvette Progesterone ELISA Using the ARS Densimeter:

Kit Contents:
   2 mL cuvettes coated with antibody and stabilized
   Plastic test tubes with caps
   1 N HCl EIA buffer
   Conjugate
   TMB Substrate
   WashSolution
   Zero Calibration Cuvette Protocol:

A volume of 1.0 ml serum is added into a plastic test tube. A volume of 500 µl of 1 N HCl is added to the plastic test tube which is then capped. The contents are mixed by gentle inversion 5 to 7 times. A volume of 500 µl of EIA buffer is added to the plastic test tube and mixed. A coated cuvette (coated with anti-progesterone antibody) is washed 5 times with wash solution. A volume of 100 µl of EIA buffer is added to the washed cuvette. A volume of 20 µl of the diluted acidified serum sample from the plastic test tube is added to the cuvette. A volume of 100 µl of conjugate is then added to the cuvette. The cuvette is capped and allowed to incubate for 1 hour and 45 minutes at room temperature. The cuvette is then inverted to empty the fluid contents and washed 5 times with Wash Solution. A volume of 1.4 ml of TMB Substrate is added to the cuvette. The cuvette is capped and allowed to incubate for exactly 30 minutes at room temperature. After incubation, the cuvette is gently inverted 5 to 7 times to make the color change homogeneous. The Zero Calibration Cuvette is placed into the Densimeter and the "Zero" button is pressed. When the display screen on the Densimeter reads"Add Sample", the Zero Calibration cuvette is removed and the test cuvette is placed into the Densimeter and the "Count" button is pressed. The Densimeter will analyze the color change and display the results as either percent (%) light transmission or the concentration of progesterone in ng/ml.

Coating of Cuvettes and Stabilization

An aliquot of 1:10 antiserum is diluted with coating buffer to a working concentration of 1:5000. A volume of 200 µl of the diluted antibody is added to each cuvette. The cuvette is tapped gently to distribute antiserum evenly over the bottom of the cuvette. The cuvettes are capped and allowed to incubate for 48 hours at 4° C. Subsequently, the cap is removed, the Cuvettes are inverted to remove fluid contents, and then washed 5 times with Wash Solution. A volume of 200 µl StabilCoat® is added into each cuvette and allowed to incubate for 30 minutes at room temperature. The cuvettes are inverted to empty the fluid contents and tapped firmly on a paper towel. The cuvettes are dried completely in an oven at room temperature and less than 15% humidity. A pan of dessicant rocks are placed in the oven to absorb moisture. The cuvettes are subsequently capped and packaged in a sealed plastic bag along with a dessicant pack.

Assay Characteristics

The specificity is the lack of interference from substances other than the parameter being measured, in this case progesterone. The % cross reactivities of the anti-progesterone antibody used were tested by the UC Davis Endocrinology Laboratory and are shown below in Table 1.

TABLE 1

| Anti-Progesterone (R4859) Antibody raised against 11α-hemisuccinate progesterone | |
| --- | --- |
| Cross-Reacting Steroids | % Cross Reaction |
| Progesterone | 100.00 |
| 11α-OH-Progesterone | 40.00 |
| 5α-Pregnane-3,20-dione | 12.19 |
| 17α-OH-Progesterone | 0.38 |
| 20α-OH-Progesterone | 0.13 |
| 20β-OH-Progesterone | 0.13 |
| Pregnanediol | <0.01 |
| Pregnenolone | 0.12 |
| Estradiol 17β | <0.01 |
| Estrone | <0.01 |
| Testosterone | <0.01 |
| Cortisol | <0.04 |

*Tested by UC Davis Endocrinology Laboratory

Sensitivity is the assay's capacity to measure the smallest amount of ligand under normal conditions. Sensitivity was calculated to be two standard deviations from the 0 ng/ml concentration on the standard curve. In the direct ELISA assay it was determined to be 0.018 ng/ml or 18 pg/ml.

Precision is known as the reproducibility of a given set of measurements for the same sample within the same run or between runs. The precision of the direct ELISA assay is reported as the coefficients of variation. The intra-assay coefficients of variation were categorized using high (8 ng/ml), medium (4 ng/ml) and low progesterone (2.0 ng/ml) serum samples since the sensitivity varies depending on the concentration of progesterone measured. The values were 8.7%, 8.4%, and 11.2% respectively. The inter-assay coefficients of variation were also categorized using high, medium and low progesterone serum samples. They were 10.2%, 11.7%, and 3.6%, respectively.

Figure 2:
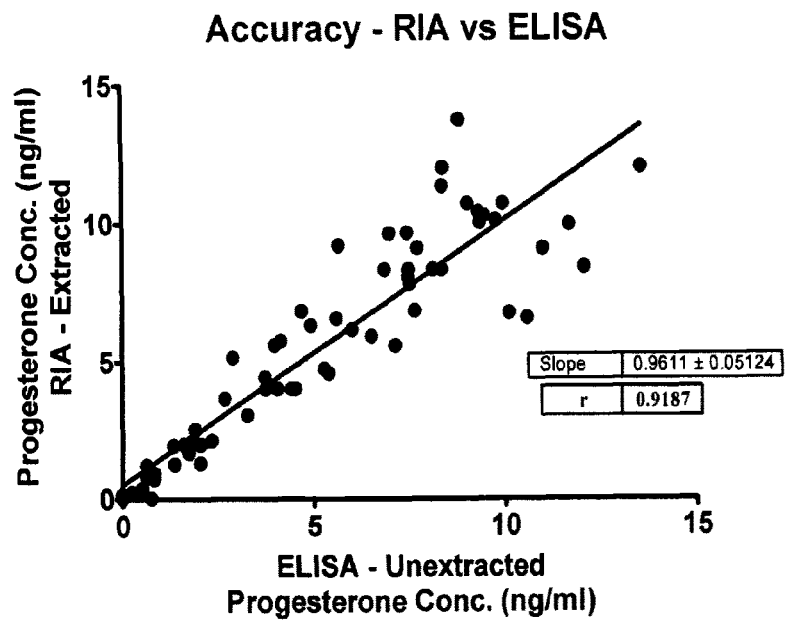
FIG. 2 shows the correlation and slope between RIA values (extracted) and direct ELISA values.
Figure 3:
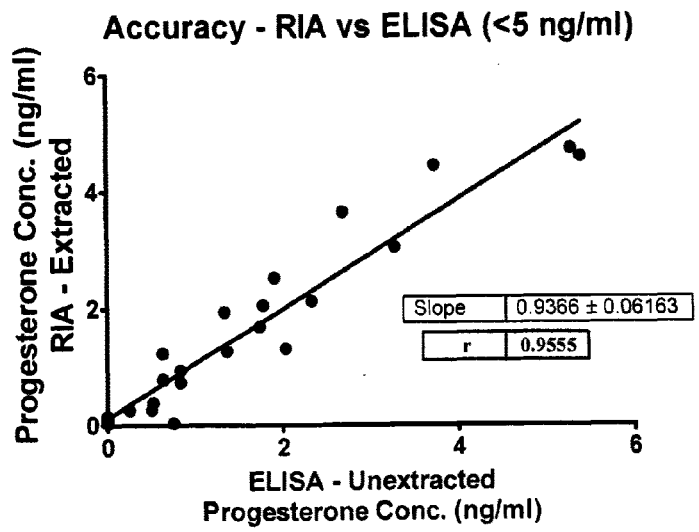
FIG. 3 shows the correlation and slope between RIA values (extracted) and direct ELISA values for samples less than 5 ng/ml.

Accuracy is the extent of agreement between the measurement of a particular ligand and the true amount of ligand present in the sample. This requires the ligand to be measured by a procedure other than the test immunoassay technique. Therefore direct ELISA values were compared to RIA (extracted) as this is often considered a gold standard, however the true gold standard is mass spectrometry. Accuracy of an assay is characterized by a high correlation and a line with a slope near 1.0. FIGS. 2 and 3 show the correlation and slope that correspond to the direct ELISA assay. FIG. 2 shows the correlation (r=0.92) between a large number of samples compared between the direct ELISA and RIA extracted values. FIG. 3 shows the high correlation (r=0.95) between the ELISA (unextracted) assay and RIA extracted values for RIA values less than 5 ng/ml. This is the concentration of greatest interest in clinical equine endocrinology. One would like to be able to assess the function of a corpus luteum or tell if a pregnant mare has a progesterone concentration greater than or less than 4 ng/ml. Progesterone levels greater than 5 ng/ml are of somewhat less importance as this simply tells that a CL is present, functional and that concentrations are adequate for the maintenance of pregnancy.

Figure 4A:
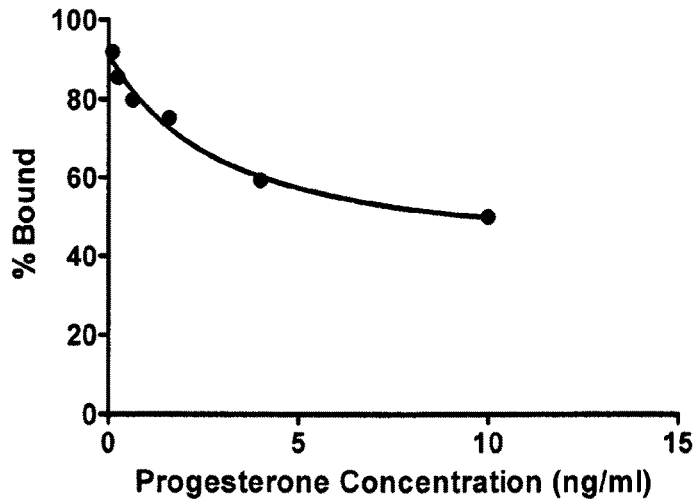
FIG. 4A shows the binding curve for the original double antibody ELISA assay and homologous combination of antibody and conjugate. Note the lack of sensitivity as the curve is moderately flat between 0 and 10 ng/ml.
Figure 4B:
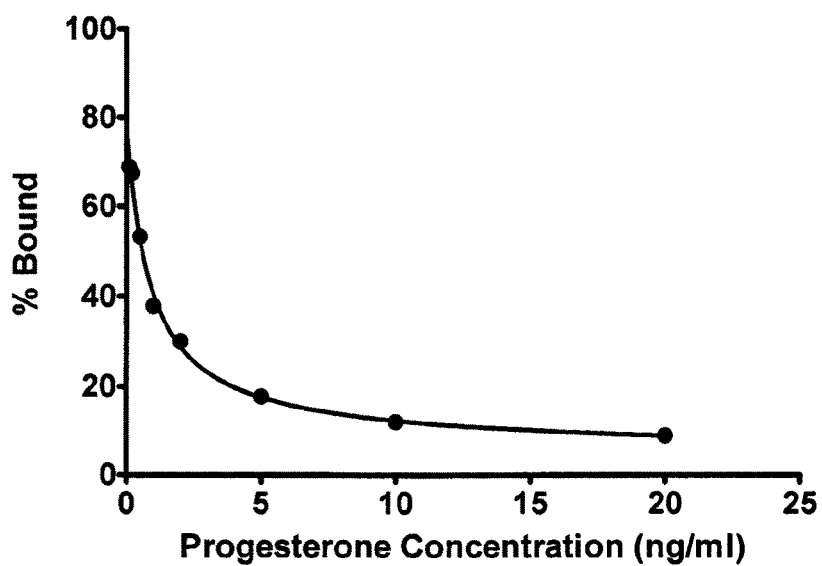
FIG. 4B shows the binding curve for the extracted ELISA assay. Note the increased sensitivity in extracted ELISA employing a heterologous combination of antibody and conjugate.

Numerous parameters were evaluated and subsequently changed in development of the direct ELISA assay. The antibody of choice is a single rabbit anti-progesterone antibody raised against the 11α-hemisuccinate position. The conjugate employed was a progesterone 3-CMO HRP providing a heterologous combination between antibody and conjugate and thus increasing sensitivity. See FIGS. 4A and 4B. The substrate was changed from an ABTS to a TMB for convenience and practicality of the commercial end result. Sensitivity of the assay was not adversely affected by this change.

Figure 5:
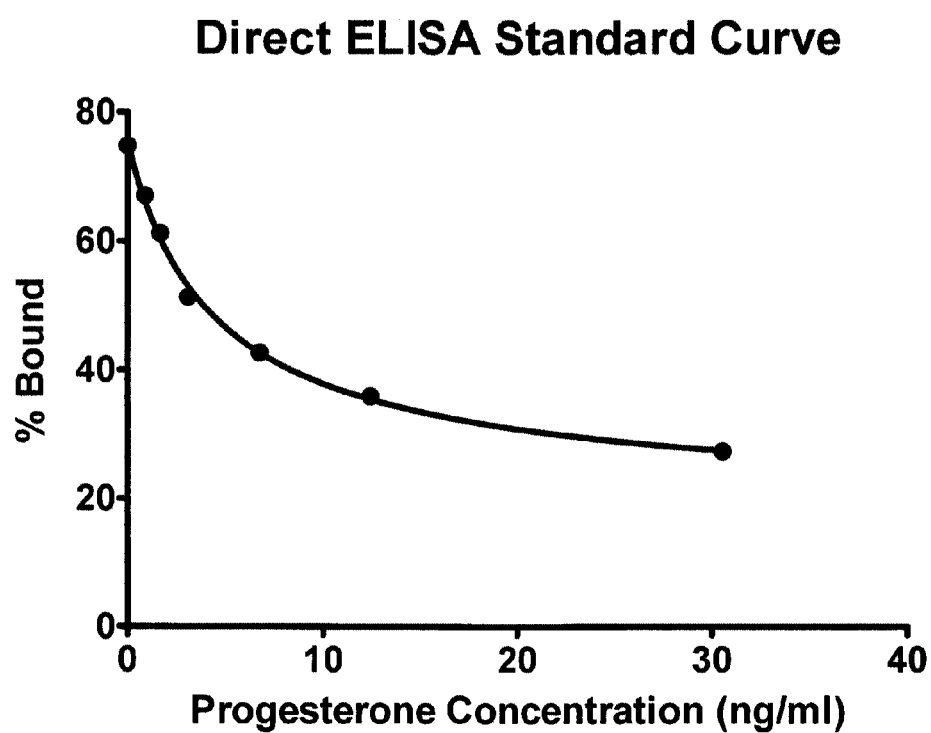
FIG. 5 shows a binding curve for the direct (single antibody) ELISA. Note the increased sensitivity in the direct ELISA employing a heterologous combination of antibody and conjugate.

The lowering of serum pH (using 1 N HCl) in conjunction with low volume (10 μl of a 1:1 dilution) was employed to avoid extraction. Progesterone concentrations in the ELISA were very close to those obtained by RIA when using 500 μl 1 N HCl. Standard curve of the direct ELISA with 500 μl HCl is shown in FIG. 5.

The assay using 500 μl of 1 N HCl and then diluting the mixture 1:1 with EIA buffer was performed multiple times to insure repeatability. The modified assay proved to be repeatable and results were highly correlated to RIA values. A direct protocol was thus developed which avoided the need to extract the progesterone from the sample and drastically lowered the volume of serum required.

Through comprehensive research to avoid organic solvent extraction, it was determined that the combination of a low volume of serum used in the assay (10 μl of a 1:1 dilution between serum and EIA buffer) and low serum pH (500 μl 1N HCl added to 1.0 ml serum) would allow for direct (non-extracted) assay of progesterone and provide accurate and repeatable results. The assay was further validated and shown to provide accurate measurement of progesterone in both serum and plasma.

The direct ELISA assay was adapted for use in cuvettes as described below. The minimum final total volume of fluid in the cuvettes required to enable the densimeter to adequately evaluate % light transmission in a sample is 1.3 ml. In initial trials with TMB substrate various proportions of EIA buffer and TMB were evaluated to achieve a 1.3 ml volume. However, it was found that the combination of the two caused a precipitate which adhered to the polystyrene wall of the cuvettes and thus interfered with light transmission. It was subsequently determined that the addition of 1.4 ml TMB substrate alone in the absence of EIA buffer was successful. It is currently recommended that the solution be mixed at the end of the incubation period to make the color change homogeneous throughout the cuvette before the % light transmission is measured.

Antibody Coating

Figure 6:
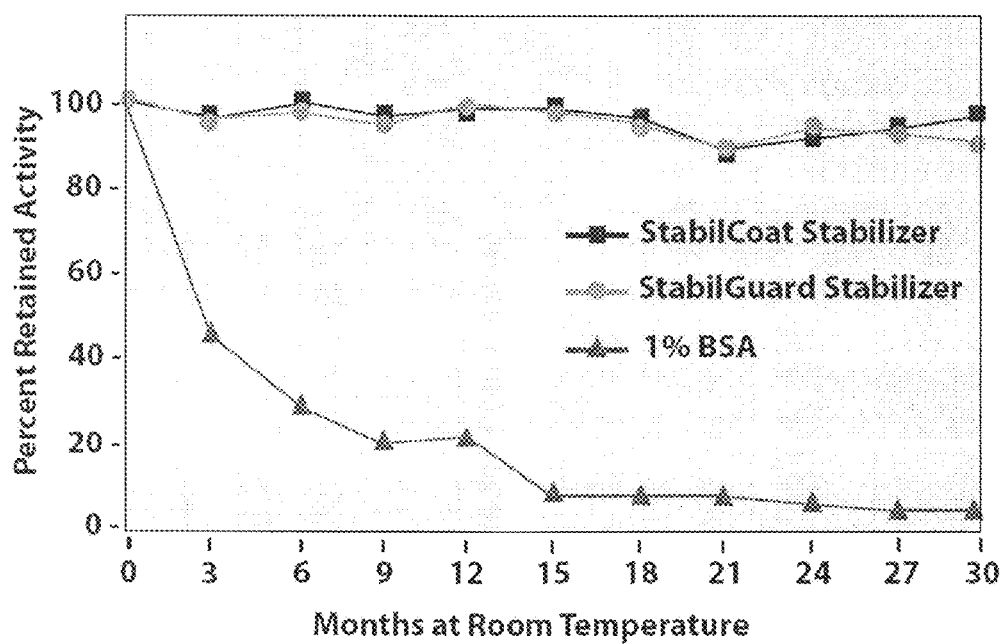
FIG. 6 shows the percent activity when StabilCoat® is used as an immunoassay stabilizer. Compare the percent retained activity for StabilCoat® vs. 1% BSA which is the absence of a stabilizer. (Adapted from Surmodics, Inc.)
Figure 7:
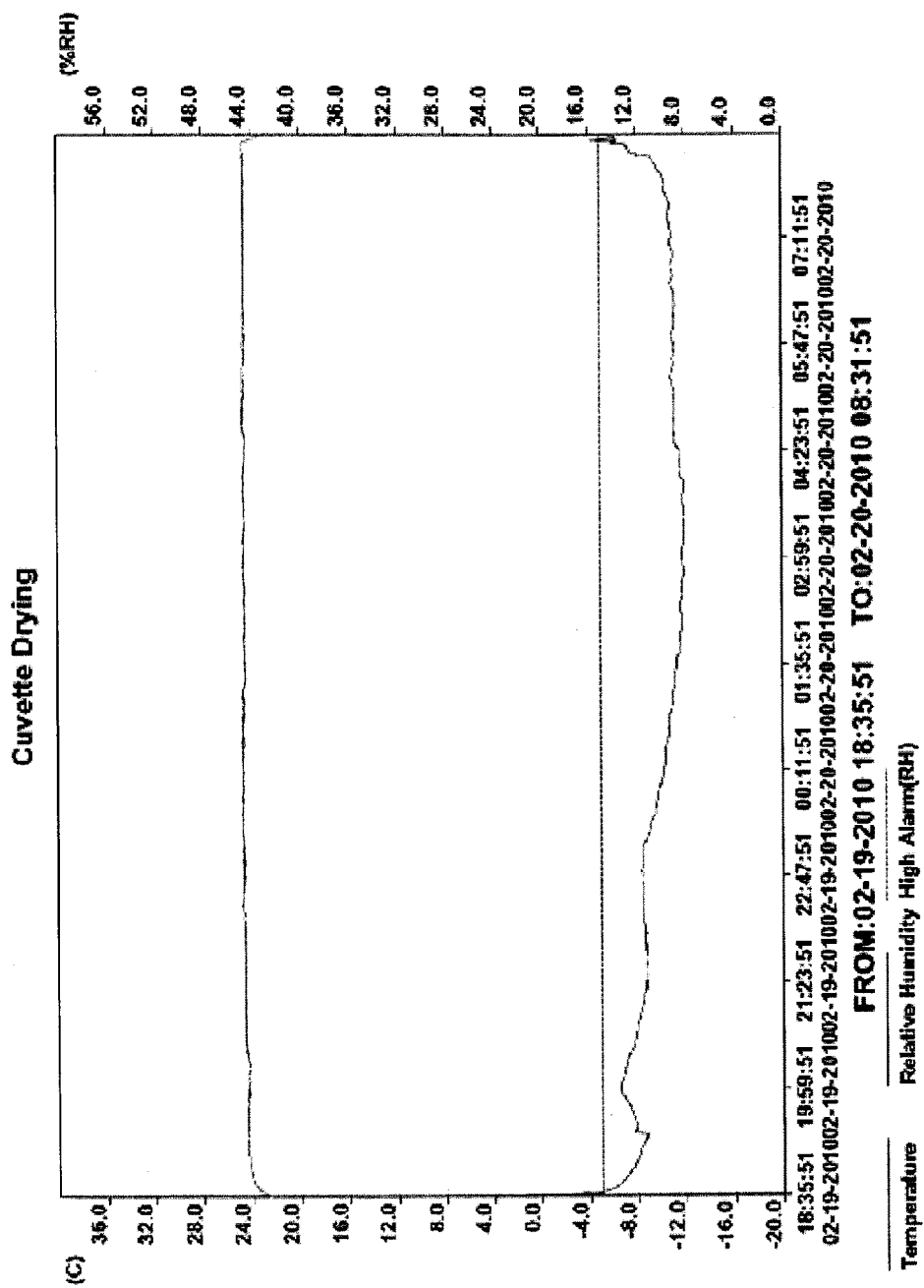
FIG. 7 shows the temperature and humidity logged when drying cuvettes. The top red line represents temperature and is shown on left y-axis and bottom blue line represents humidity and is shown on the right y-axis.
Figure 8:
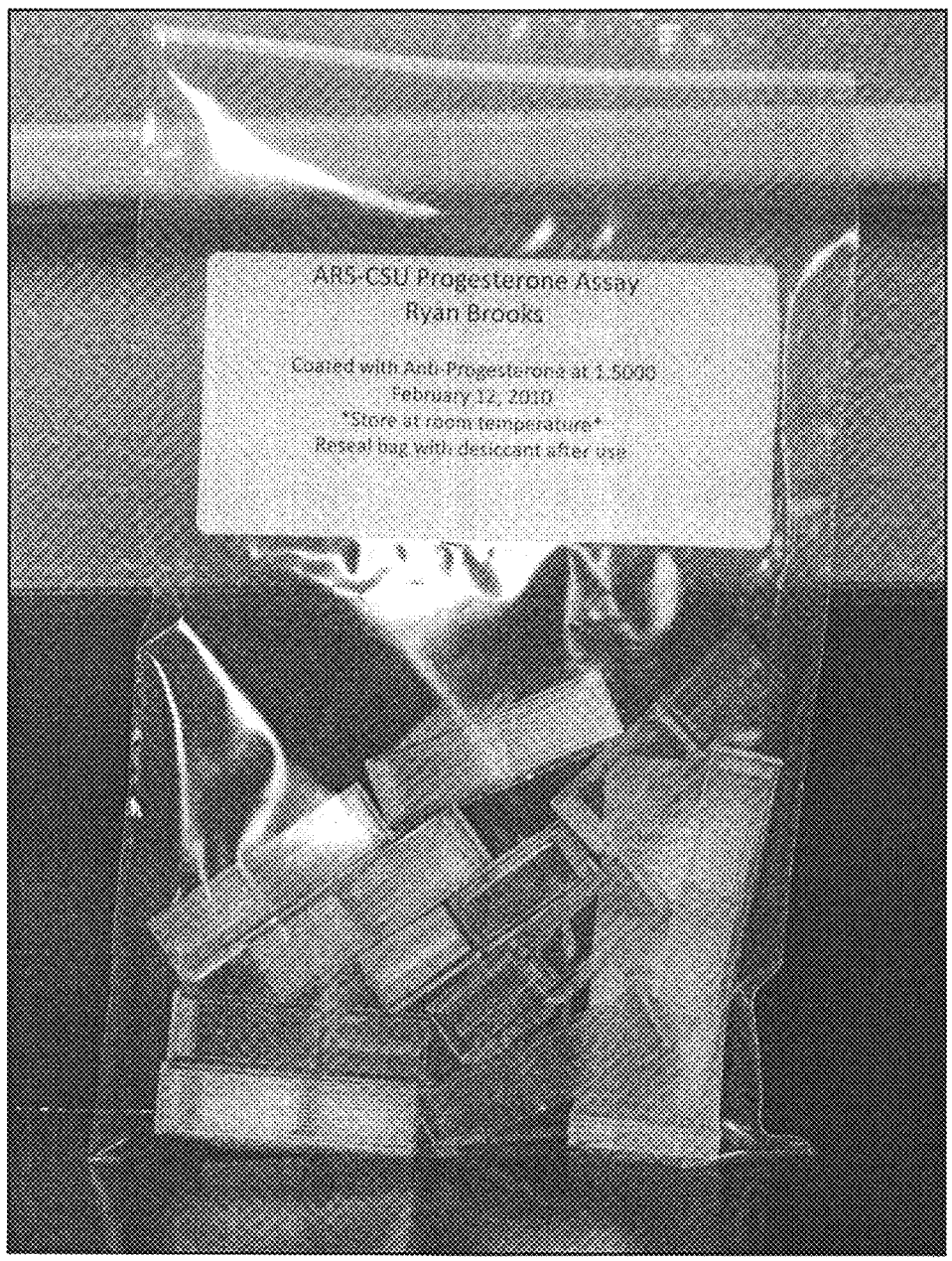
FIG. 8 shows the packaging of cuvettes once stabilized with StabilCoat® and packaged with a desiccant pack.

Coating of cuvettes with anti-progesterone antibody was evaluated. Cuvettes were coated at the same 1:5,000 dilution of anti-progesterone antibody used in the 96-well plates. However, cuvettes were coated with 200 μl instead of the 50 μl used in the 96-well plate. Once plates or cuvettes are coated, they were incubated at 4° C. for a minimum of 24 hours. The coated plates or cuvettes were used for a maximum of 3 to 4 weeks at which time the antibody begins to degrade. This would not be conducive to batch production and shipment of cuvettes to the consumer to be used over an entire breeding season. Therefore, the use of an immunoassay stabilizer was evaluated as a potential solution. The stabilizer would allow coated cuvettes to be stored dry, at room temperature for up to 30 months with near 100% antibody activity, (FIG. 6). In theory, cuvettes could be coated with 200 μl anti-progesterone antibody, incubated for 48 hours at 4° C., inverted to remove the fluid, and washed 5× with a wash buffer. A volume of 200 μl of StabilCoat® [Surmodics, Eden Prairie, Minn.] stabilizer would be added to the cuvette and allowed to incubate for 30 minutes. The cuvette would then be emptied and dried in an oven at approximately room temperature with less than 15% humidity (FIG. 7). Cuvettes would then be capped and packaged in a bag with a desiccant (FIG. 8).

Complete Assay Kit

Figure 9:
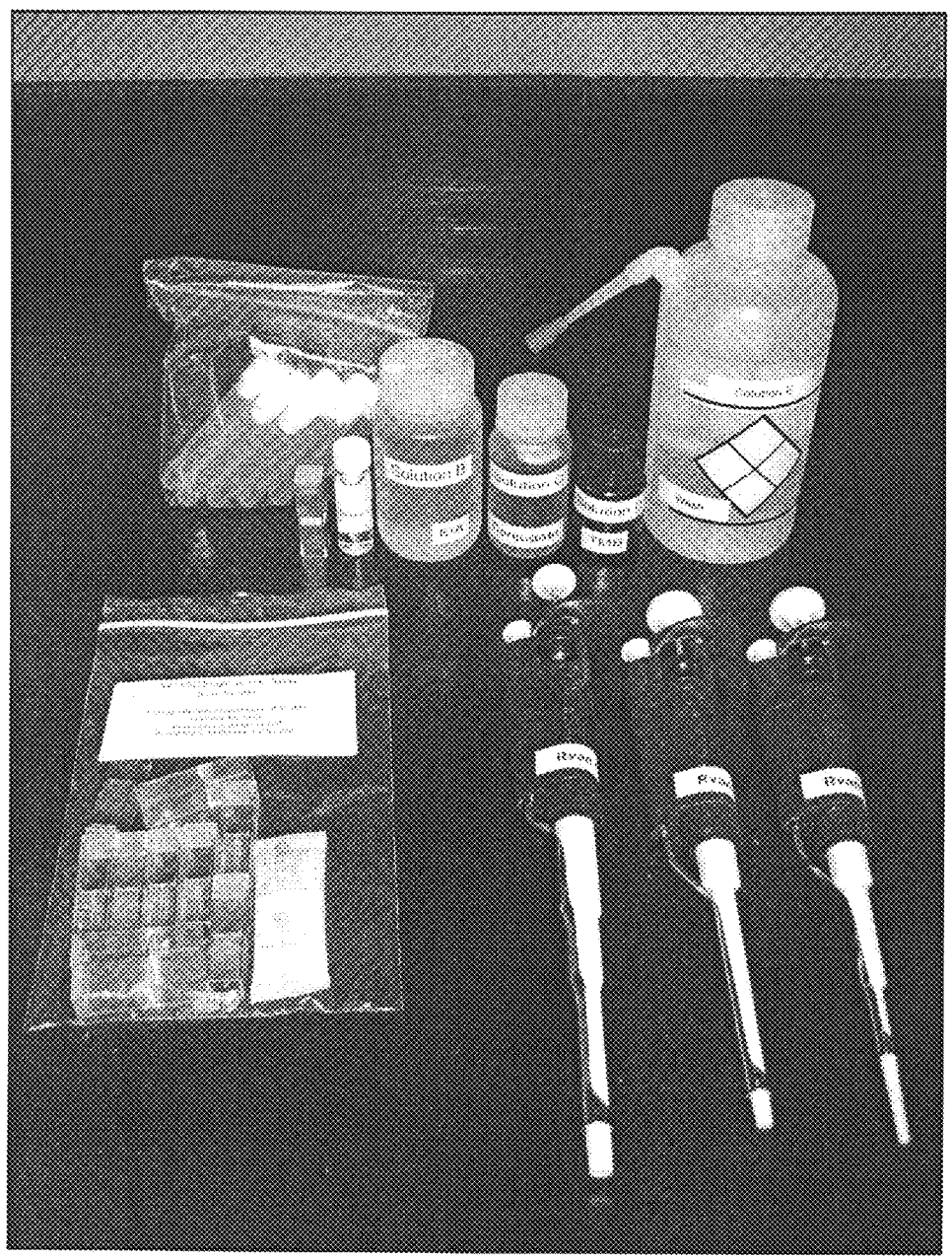
FIG. 9 shows the components of a kit suitable for practice of the present invention.
Figure 10:
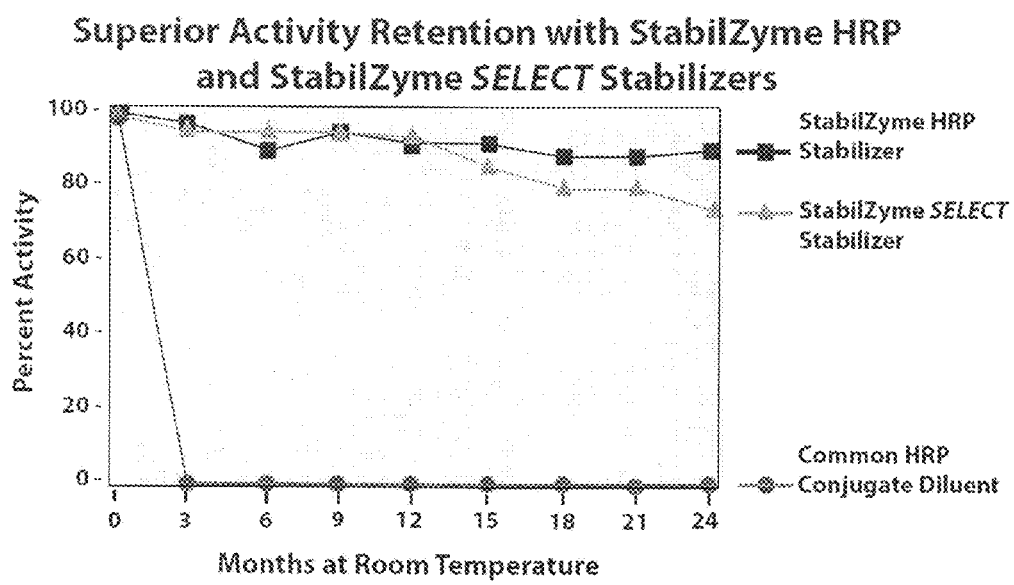
FIG. 10 shows percent activity of HRP Conjugate when stabilized with StabilZyme®. (Adapted from Surmodics, Inc.)
Figure 11:
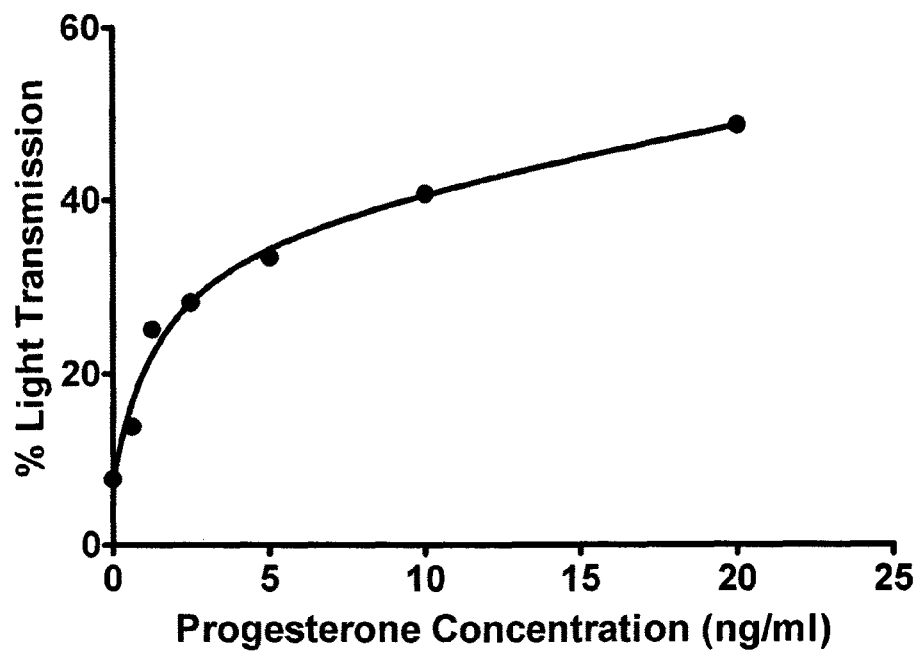
FIG. 11 shows a standard curve for the direct progesterone ELISA comparing progesterone concentration (ng/ml) with % light transmission.

A progesterone ELISA kit was designed that could be used in a commercial spectrophotometer (i.e. the ARS Densimeter). The kit contained all solutions and materials needed to run the direct (non-extracted) progesterone ELISA assay (FIG. 9). The progesterone-HRP conjugate was stabilized at a working concentration of 1:200,000 with the product StabilZyme® [Surmodics, Eden Prairie, Minn.]. This would eliminate user error when making the working dilution of conjugate as well as rendering the conjugate stable for approximately two years (FIG. 10). Several trials were run to insure that all components of the kit had a good efficacy and yielded progesterone concentrations in equine serum samples that were correlated with RIA values. Standards were run in the cuvettes and read in the ARS densimeter to show that the antibody would bind, produce a color change and appropriate a standard curve (FIG. 11).

EXAMPLE 2

Clinical Applications

In breeding management of the mare there are many clinical applications for the use of a progesterone assay. Several applications for non-pregnant and pregnant mares are discussed below:

Non-Pregnant Mares

Normal Luteal Values

Estrus lasts approximately 4 to 7 days in a mare while diestrus lasts roughly 14 to 15 days. Progesterone concentrations begin to rise 12 to 24 hours post ovulation and peak within 5 to 6 days after ovulation. Average progesterone concentrations between days 5 and 14 were 6-10 ng/ml. Luteolysis, or regression of the CL does not occur until approximately day 14 or 15 at which point progesterone concentrations decline dramatically. A corpus luteum will not respond to prostaglandin administration until approximately 5 days post ovulation. If the presence of a CL cannot be confirmed by ultrasound one can perform a progesterone assay and use the value obtained to determine if a CL is present.

Confirming Ovulation in Cycling Mare

In a small percentage of mares throughout each breeding season we are unable to confirm ovulation by ultrasonography. A large follicle will have been noted during estrus, the mare will have been bred and upon examination 1 to 2 days later no large follicle is present but also no collapsed follicle or corpus hemorrhagicum and subsequently no corpus luteum. A blood sample may be taken 2 to 3 days after disappearance of a large follicle for a progesterone assay. If concentrations are above 1 ng/ml, luteal tissue is present and ovulation most likely occurred. Another sample 1 to 2 days later should show an increase in progesterone concentrations and verify the diagnosis.

Anovulatory Follicles

Progesterone concentrations may be used to determine the luteal status of anovulatory follicles. A majority of anovulatory follicles (approximately 85%) eventually luteinize and produce moderate to large amounts of progesterone (31). Prostaglandins, administered 9 to 10 days after the first observation of echogenic particles or strands within the follicular lumen, will induce regression of the luteinized anovulatory follicle (31). However, if we can assess the progesterone concentration and determine if the anovulatory follicle is an LAF we can administer prostaglandins at an earlier time as it has been shown by McCue and Squires (2002) that luteinized anovulatory follicles will respond to prostaglandins and show a decline in progesterone to less than 1 ng/ml within 48 hours (31).

Mares that Cannot be Palpated Per Rectum

There is great advantage for using a progesterone assay in reproductive management of the estrous cycle of a mare that cannot be palpated per rectum due to a previous rectal tear, small physical size, or adverse behaviors that do not permit palpation per rectum. Teasing may be used in conjunction with daily progesterone samples to determine when to breed and estimate the day of ovulation. Daily blood samples should be collected beginning shortly after the onset of behavioral estrus and continue until approximately one day after behavioral estrus subsides. Knowing the day of ovulation is very important in potential management of twins in a mare that carries her own pregnancy and the day of a flush in an embryo transfer mare. Progesterone concentrations will be less than 1 ng/ml during estrus and begin to rise significantly 12 to 24 hours after ovulation. Evaluation of serial progesterone concentrations will allow for the determination of the day of ovulation and the subsequent 14 day pregnancy exam or embryo flush procedure.

Transitional Mare

Management of the transitional mare can be enhanced by sampling of progesterone concentration. To determine when a mare has ended the spring transition period and ovulated for the first time in a given season, a progesterone sample may be taken once weekly (or more if desired) instead of constantly palpating per rectum. Progesterone concentrations above 1 ng/ml indicate that luteal tissue is present and that the mare has ovulated. Once a mare has ovulated in the spring, she will generally continue to ovulate at 21-day intervals throughout the physiologic breeding season.

Evaluate Therapy of Native P4

Native progesterone therapy may be evaluated by performing a progesterone assay. Administration of a short- or long-acting form of natural progesterone should cause a transient (ie. 24 hours) or prolonged (ie. 10 to 14 days) rise in serum progesterone levels. In contrast, Regu-mate® or altrenogest will not be detected in a conventional progesterone assay. This synthetic progestin does not cross-react with the antibody used in progesterone assays. This can be advantageous in a pregnant mare receiving supplementation as one can continue to supplement with altrenogest and also assay for endogenous progesterone at various time points (ie. after formation of secondary corpora lutea) and determine if therapy can be discontinued.

Embryo Transfer Recipients

The level of serum progesterone may be used as another criterion when evaluating recipients for embryo transfer. Currently, most facilities assess the normality of the recipients cycle, tone of the uterus and cervix, presence of corpora lutea, and absence of uterine edema or free fluid within the lumen of the uterus. Progesterone samples may be another parameter used as low progesterone often correlates with poor tone or an inadequate CL. This could become a routine assessment on 5-day checks of recipient mares.

Pregnant Mares

Confirm P4 Levels

Progesterone is most frequently assayed in pregnant mares to determine if the mare is producing adequate progesterone to maintain pregnancy. Clinically, a mare may arrive for an ultrasound pregnancy exam and upon examination has a small CL or no CL, slight uterine edema and/or poor tone in the uterus. At this time we would recommend submission of a blood sample for progesterone analysis. The initial pregnancy examination is most commonly performed 14 to 16 days after ovulation during the period of maternal recognition of pregnancy. Beyond day 40 of gestation progesterone values may increase due to formation of secondary/accessory corpora lutea. At around 70-90 days of gestation the placenta takes over the role of progesterone production and by day 100 supplementation is no longer needed. Some owners may keep high-risk mares on exogenous progesterone treatment for the entire duration of pregnancy. Typically, if the serum progesterone level is ≥4 ng/ml a mare is considered able to maintain pregnancy. If endogenous progesterone levels are less than 4 ng/ml during the first trimester when ovarian corpora lutea are responsible for maintenance of pregnancy, exogenous progestin supplementation would then be advised. Regu-Mate® and compounded long-acting natural progesterone are the two most common formulations used to supplement pregnant mares.

Activity of 2° CL's

One can assess the activity of secondary corpora lutea in pregnant mares by performing a progesterone assay. Endometrial cups form around day 35 of pregnancy and produce the luteotropin eCG which subsequently causes the formation of secondary/accessory corpora lutea in most mares. After approximately day 40 of gestation, a further rise is serum progesterone levels should be seen indicating the presence of 2° CL's.

Prior to Foaling

Progesterone concentrations may possibly be used as an indicator of impending parturition. Progesterone levels begin to rise about 310 days of gestation and dramatically decline just prior to parturition. In one mare sampled in the current study, progesterone concentrations were high (>25 ng/ml) until one day prior to foaling at which time levels dropped to around 16 ng/ml and continued to decline until the mare foaled. (FIG. 3.1) A potential clinical use of the progesterone assay may be in maiden mares that fail to "bag up" and therefore do not have sufficient "milk" to allow tests such as milk calcium to be performed. Detection of a sharp decline in progesterone levels could a valuable tool to predict the time of foaling in these pregnant mares.

Failure of Maternal Recognition of Pregnancy Maternal recognition of pregnancy fails to occur in a number of mares. However, if this is determined early enough we are able to save the pregnancy with exogenous progesterone supplementation. If a mare is examined at 14 days after ovulation and a small CL is observed along with an embryonic vesicle, by 16 days the CL is often no longer visible. Regression of the corpus luteum results in decline in the production of progesterone and subsequent loss of the pregnancy. Affected mares are supplemented with exogenous progesterone if the CL is thought to be of poor quality. However, a blood sample could be collected to determine if endogenous progesterone is truly deficient and whether supplementation is truly needed.

CONCLUSION

In accordance with the present invention, a quantitative and sensitive progesterone ELISA assay has been developed suitable for use on non-extracted equine serum or plasma. In order to achieve the sensitive ELISA assay, a single anti-progesterone antibody was employed that provided a heterologous combination between antibody and HRP conjugate. The antibody was obtained from antiserum after immunization of New Zealand white rabbits with progesterone 11α-hemisuccinate-BSA and purification to remove anti-BSA. The conjugate is HRP coupled to a 3-CMO derivative of progesterone. This heterologous combination provided a sensitive and quantitative assay. A TMB substrate was selected over an ABTS substrate as it provided a more practical application for the commercial utilization. A protocol was developed to free progesterone from serum binding proteins (ie. CBG and albumin) and therefore bypass the need for organic solvent extraction. Hydrochloric acid was used to lower serum pH and denature albumin and CBG thus freeing progesterone from binding proteins for subsequent assay. A low volume of serum was used in the assay as this eliminated interference caused by non-specific serum proteins binding to the antibody. The end volume analyzed was 10 µl of a mixture of 1.0 ml serum, 500 µl 1N HCl, and 500 µl EIA buffer. This volume did not influence the sensitivity of the assay. The new direct (non-extracted) ELISA had a high correlation (r=0.9555 at P4 concentrations <5 ng/ml) with a traditional RIA that requires organic solvent extraction, a sensitivity of 0.018 ng/ml, and intra- and inter-assay coefficients of variation of 11.2% and 3.6%, 8.4% and 11.7%, and 8.7% and 10.2% for progesterone concentrations of 2.0, 4.0, and 8.0 ng/ml, respectively.

The ELISA was also converted from a 96-well plate format to a single cuvette system thus allowing quantification by a commercially available spectrophotometer. This was achieved by coating cuvettes and performing the assay as initially developed for the 96-well plate with slight increases in volumes of components. Cuvettes and conjugate were used in conjunction with immunoassay stabilizers to provide a longer shelf life, ease of use and ease of shipment of the commercial product. An assay kit and protocol were developed that contained all components needed to perform the direct progesterone ELISA and quantify results with use of the ARS Densimeter. A standard curve was tested to verify sensitivity and appropriate binding in the cuvette system. The main clinical applications of the progesterone ELISA are 1) determination of the presence or absence of active luteal tissue in non-pregnant mares and 2) determination of progesterone levels in pregnant mares. Other potential applications include diagnosis of specific types of ovarian pathology (ie. persistent corpus luteum and luteinized anovulatory follicles) and prediction of impending parturition.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A direct competitive enzyme linked immunoabsorbent assay (ELISA) for determining progesterone concentration in a sample taken from an equine test subject, comprising:
   a) providing in at least one container immobilized antibody that specifically binds to and is specific for progesterone;
   b) obtaining at least one plasma or serum sample from said test subject,
   c) treating each of said plasma or serum sample(s) by (i) mixing a volume of the sample with a volume of acid which reduces the pH of the sample to about 4 thereby releasing progesterone from cortisol binding globulin and albumin present in said sample, and (ii) adding to the acidified sample a volume of assay buffer, the combined volumes of said buffer and said acid being equal to the volume of said sample before acidification, thereby providing a 1:1 dilution of the treated sample;
   d) contacting the immobilized antibody in one of said container(s) with an aliquot of one of the treated sample (s) resulting from step c), said aliquot having a volume sufficiently low to provide accuracy and precision of the assay;
   e) introducing into the sample-contacted container(s) a known amount of tracer reagent, in solution, comprising progesterone operably linked to an enzyme, the progesterone moiety of the tracer reagent capable of being specifically bound by the immobilized antibody and said linked enzyme moiety capable of producing a detectable signal indicative of progesterone concentration when reacted with a substrate therefor;
   f) incubating the contents of the sample container(s) under conditions promoting competitive binding of progesterone in the tracer reagent and treated sample(s) to said immobilized antibody;
   g) removing unbound tracer reagent, if any, from the contents of the sample container(s) after step f) via washing;
   h) adding said substrate to the washed container(s) of step g);
   i) measuring the detectable signal(s) produced in the container(s) of step h) from the enzyme-substrate reaction (s); and
   j) correlating the measured detectable signal(s) with at least one standard containing a known concentration of progesterone, thereby determining the progesterone concentration in each of said sample(s).

2. The assay of claim 1, wherein the immobilized antibody is an affinity-purified rabbit anti-progesterone antibody raised against progesterone 11α-hemisuccinate-bovine serum albumin (BSA).

3. The assay of claim 1, wherein the tracer reagent comprises horseradish peroxidase (HRP) conjugated to a 3-O-carboxymethyloxime (3-CMO) derivative of progesterone.

4. The assay of claim 1, wherein the substrate is a tetramethylbenzidine (TMB) substrate and said enzyme is streptavidin horse radish peroxidase.

5. The assay of claim 1, wherein said acid is 1N HCl.

6. The assay of claim 1, wherein the container is a cuvette in which said antibody is immobilized.

7. The assay of claim 6, wherein said assay determines progesterone concentration in a range of 0 to 20 ng/ml.

8. The assay of claim 6, wherein the detectable signal(s) are measured by placing said cuvette(s) in a spectrophotometer.

9. The assay of claim 1, wherein the antibody is immobilized in wells of a microtitre plate.

10. The assay of claim 1, wherein step d) and step e) are carried out simultaneously.

11. The assay of claim 1, wherein step d) and step e) are carried out sequentially.

12. The assay of claim 1, wherein the aliquot volume in step d) is 0.5% of the volume of the treated sample resulting from step c).

13. The assay of claim 1, wherein correlating the detectable signal(s) with the concentration of progesterone in at least one standard is by reference to a standard curve.

14. The assay of claim 13, wherein the standard curve is derived from a series of standard solutions determined in the manner of steps c-i), with each standard solution containing a different predetermined concentration of progesterone within a range of 0-20 ng/ml.

15. The assay of claim 1, wherein the assay determines progesterone concentration in a range of 0 to 4 ng/ml.

16. The assay of claim 1, wherein the concentration of progesterone determined in each of said sample(s) is compared to a predetermined progesterone concentration level associated with a parameter selected from the group consisting of normal equine luteal values, confirmation of ovulation, presence or absence of anovulatory follicles, identification of transitional mares, evaluation of progesterone augmentation therapies, evaluation of embryo transfer recipients, evaluation of progesterone levels in pregnant mares, activity of secondary corpora *lutea*, and failure of maternal recognition of pregnancy.

* * * * *